United States Patent
Rudko

Patent Number: 6,132,422
Date of Patent: Oct. 17, 2000

[54] HANDPIECE FOR TRANSMYOCARDIAL VASCULARIZATION HEART-SYNCHRONIZED PULSED LASER SYSTEM

[75] Inventor: Robert I. Rudko, Holliston, Mass.

[73] Assignee: PLC Medical Systems, Inc., Milford, Mass.

[21] Appl. No.: 08/201,052

[22] Filed: Feb. 24, 1994

Related U.S. Application Data

[63] Continuation of application No. 08/014,363, Feb. 5, 1993, abandoned, which is a continuation of application No. 07/928,531, Aug. 13, 1992, abandoned, which is a continuation of application No. 07/586,891, Sep. 24, 1990, abandoned.

[51] Int. Cl.[7] ................................................. A61B 17/36
[52] U.S. Cl. ................................................ 606/7; 606/17
[58] Field of Search ................................. 606/7, 10–19

[56] References Cited

U.S. PATENT DOCUMENTS

| | | | |
|---|---|---|---|
| 1,147,408 | 7/1915 | Kells | 604/164 |
| 1,562,460 | 11/1925 | Fee | 606/49 |
| 1,934,046 | 11/1933 | DeMarchi | 604/115 |
| 3,865,113 | 2/1975 | Sharon et al. | 606/18 |
| 3,913,582 | 10/1975 | Sharon | 606/10 |
| 4,266,548 | 5/1981 | Davi | 606/17 |
| 4,723,940 | 2/1988 | Wiegernck | 604/115 |
| 4,757,515 | 7/1988 | Hughes | 372/109 |
| 4,850,352 | 7/1989 | Johnson | 606/13 |
| 4,940,411 | 7/1990 | Vassiliadis et al. | 433/215 |
| 5,057,085 | 10/1991 | Kopans | 604/164 |
| 5,176,648 | 1/1993 | Holmes et al. | 604/164 |

FOREIGN PATENT DOCUMENTS 0153908  12/1980  Japan.

*Primary Examiner*—Michael Peffley
*Attorney, Agent, or Firm*—Iandiorio & Teska

[57] ABSTRACT

A handpiece for use in transmyocardial revascularization heart-synchronized pulsed laser system includes a barrel having a passage for transmitting a laser beam; a surface at the distal end of the barrel for contacting the wall of the heart; an aperture located at the distal end of the barrel and the enlarged surface for transmitting the laser beam; and means for focusing the laser beam proximate to the aperture to vaporize the tissue of the heart wall and create a hole to the interior heart chamber.

18 Claims, 2 Drawing Sheets

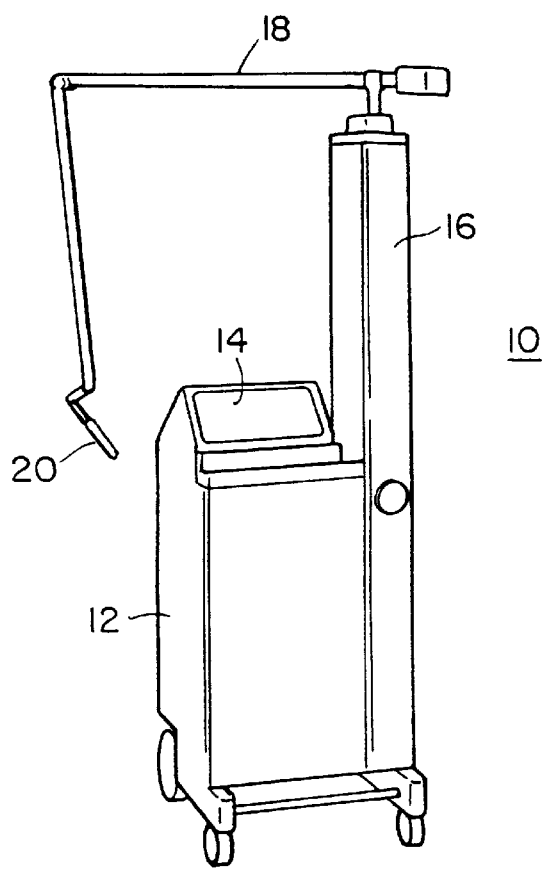
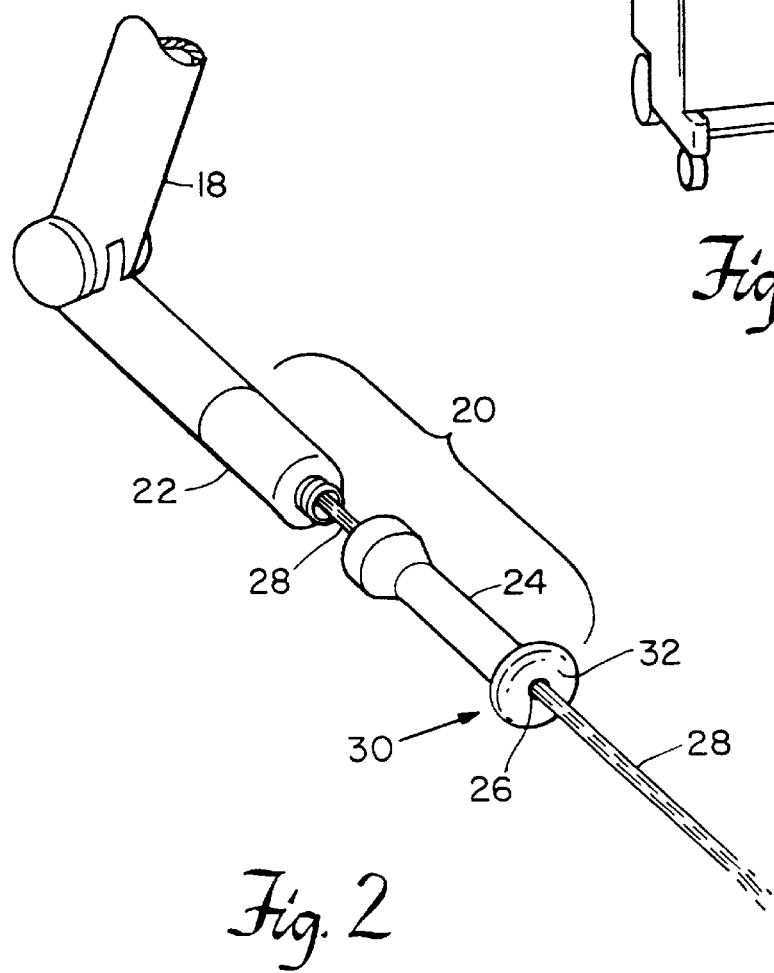

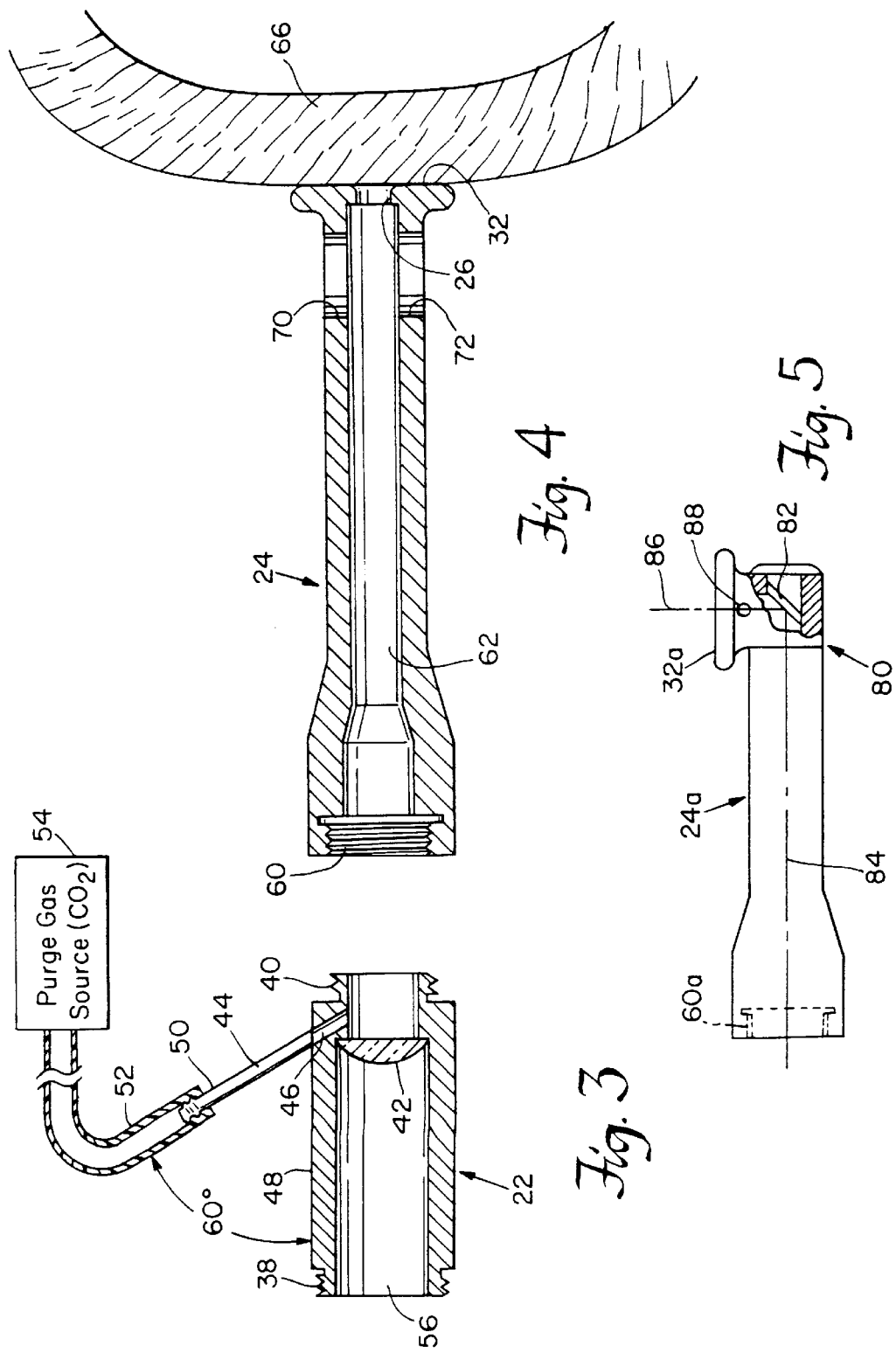

HANDPIECE FOR TRANSMYOCARDIAL VASCULARIZATION HEART-SYNCHRONIZED PULSED LASER SYSTEM

This is a continuation of application Ser. No. 08/014,363, filed Feb. 5, 1993 (now abandoned) which is a continuation of application Ser. No. 07/928,531, filed Aug. 13, 1992 (now abandoned) which is a continuation application of Ser. No. 07/586,891 filed Sep. 24, 1990 (now abandoned).

FIELD OF INVENTION

This invention relates to a handpiece for use in a transmyocardial vascularization heart-synchronized pulsed laser system, and more particularly to such a handpiece whose contact surface avoids destabilization of the beating heart.

RELATED CASES

This application is related to and incorporates herein by reference the following applications having common inventors and assignee and filed on even date herewith:

"Heart-Synchronized Pulsed Laser System", by Robert I. Rudko and Stephen J. Linhares, now U.S. Pat. No. 5,125,926;

"Long Pulse, Fast Flow Laser System and Method", by Robert I. Rudko, now U.S. Pat. No. 5,109,388; and "Heart-Synchronized Vacuum-Assisted Pulsed Laser System and Method", by Robert I. Rudko, now U.S. Pat. No. 5,125,924.

BACKGROUND OF INVENTION

Transmyocardial revascularization (TMR) is an alternative technique to bypass surgery for increasing blood flow to the heart muscle. It involves the puncturing of the heart wall with a laser to form a plurality of holes which heal on the outside but remain open on the inside of the heart, to provide an alternative source of blood to the heart muscle. This technique has been employed on a stilled, by-passed heart using a $CO_2$ laser with a hand-piece which rests on the heart in order to ensure that the laser beam focus occurs at the correct point on the heart. Recently, a dramatic improvement in TMR has enabled this technique to be used on a beating heart without the need to slow or still it. This has been accomplished with an innovative synchronizing approach disclosed in one or more of the U.S. patent applications listed above under Related Cases and incorporated herein by reference. However, this has introduced new problems. A beating heart is electrically active; the contact of a handpiece against the heart wall disrupts that electrical activity and interferes with the heart function. Arrhythmia and fibrillation can occur and can result in heart failure. Further, any interference with the electrical field of the heart interrupts the synchronous operation of the laser so that the laser is no longer constrained to fire at the optimum moment in the beating heart cycle. The current handpieces used with $CO_2$ lasers have a relatively sharp tip on a gauge rod extending from the end of the handpiece used to consistently position the handpiece at the proper distance from the stilled heart wall for accurate laser beam focusing and impingement. Such a tip creates increased pressure on the heart, which can cause arrhythmia, fibrillation, and can even puncture the wall of the heart. Further, with these handpieces it is difficult to maintain the laser beam perpendicular with the wall of a beating heart as is necessary to effect clean, correctly placed holes in the heart wall.

SUMMARY OF INVENTION

It is therefore an object of this invention to provide an improved laser handpiece for a heart-synchronized pulsed laser system for transmyocardial vascularization.

It is a further object of this invention to provide such a laser handpiece which more readily maintains perpendicularity with the wall of a beating heart.

It is a further object of this invention to provide such a laser handpiece which accurately locates the laser beam focal point at the correct point on the heart wall.

It is a further object of this invention to provide such a laser handpiece which reduces interference with the heart electric field and function.

It is a further object of this invention to provide such a laser handpiece which dissipates the laser plume to prevent interference with or damage to the laser beam lens.

This invention results from the realization that an effective and safe handpiece capable of contacting the wall of a beating heart to insure proper location and focus of the laser beam, yet minimize danger to or interference with the beating heart can be achieved by focusing the laser beam in the vicinity of the laser beam exit aperture at the end of the handpiece and providing a large, smooth, flat heart contact surface at that end of the handpiece to minimize pressure on an interference with the beating heart.

This invention features a handpiece for use in a transmyocardial vascularization heart-synchronized pulsed laser system including a barrel having a passage for transmitting a laser beam. There is a surface at the distal end of the barrel for contacting the wall of the heart and an aperture located at the distal end of the barrel in the enlarged surface for transmitting a laser beam. There are means for focusing a laser beam proximate to the aperture to vaporize the tissue of the heart wall to create a hole to the interior of the heart chamber. In a preferred embodiment the handpiece further includes means for introducing a gas to purge the passage, between the aperture and the means for focusing, of debris from the vaporized heart wall. There may also be exhaust means for venting the debris purged by the gas. The barrel may be straight or may be angled and include deflecting means for redirecting the laser beam along the angled barrel. The deflecting means may include a mirror. The contact surface at the distal end of the barrel is generally smooth and flat with rounded edges, and is generally greater than 1 cm in diameter. The gas may be introduced proximate the means for focusing and exhausted proximate the aperture. The beam may be focused beyond the enlarged surface, within the barrel or intermediately within the aperture.

DISCLOSURE OF PREFERRED EMBODIMENT

Other objects, features and advantages will occur to those skilled in the art from the following description of a preferred embodiment and the accompanying drawings, in which:

FIG. 1 is a three-dimensional view of a $CO_2$ surgical laser system employing the handpiece of this invention;

FIG. 2 is an enlarged view of a handpiece according to this invention and a portion of the articulated optical arm which carries it;

FIG. 3 is an enlarged cross-sectional view of the focusing lens section of the handpiece of FIGS. 1 and 2;

FIG. 4 is an enlarged sectional view of the barrel of the handpiece of FIGS. 1 and 2; and FIG. 5 is a side elevational view with portions broken away of an alternative form of barrel similar to that shown in FIG. 4.

The handpiece of this invention for use in a transmyocardial revascularization heart-synchronized pulsed laser system may be accomplished using a barrel having a passage for transmitting a laser beam. The barrel may be simply a hollow tube. There is a surface at the distal end of the barrel for contacting the wall of the heart. This surface is smooth and flat so that there are no sharp edges to probe or prick the heart wall. It is also broad in order to minimize the contact pressure between the handpiece and the heart wall and minimize interference with the operation of the heart muscle and the electrical activity of the beating heart. The handpiece, at least at its contact surface, is electrically and thermally insulating for the same purpose. There is an aperture located at the distal end of the barrel in the enlarged surface for transmitting a laser beam through to the heart wall. There are also some means for focusing the laser beam proximate to the aperture to vaporize the tissue of the heart wall and create a hole through the wall to the interior of the heart chamber. The laser may be focused at, near or beyond the aperture. There is an inlet to introduce a purging gas through the passage to purge, the aperture and the means for focusing, of debris produced by the vaporization of the heart wall by the laser beam. The means for focusing is typically a lens which is mounted in the focusing unit or lens unit associated with the barrel. There is one or more outlets proximate the distal end of the barrel through which the purged gas with the debris is vented. The barrel may be straight or may be angled. If it is angled there are suitable deflecting means such as mirrors or reflectors, to redirect the beam along the angled or curved barrel. Typically the enlarged surface for contacting the heart is 1 cm or more in diameter.

There is shown in FIG. 1 a surgical laser system 10 including a power supply 12 and control panel 14 for operating $CO_2$ laser 16, whose output beam is directed through articulated arm 18 to handpiece 20. Handpiece 20 may include a lens unit 22 including a lens for focusing the laser beam and a barrel 24 which includes an aperture 26 through which the laser beam 28 exits. The distal end 30 of barrel 24 includes an enlarged contact surface 32 for contacting the wall of the heart to be perforated by the laser beam. Surface 32 is relatively large to minimize the contact pressure between it and the heart wall, and is flat and smooth with rounded edges to minimize interference with the heart. Surface 32 is typically 1 cm or greater in diameter, and may be electrically and thermally insulating.

The focusing unit or lens unit 22, FIG. 3, includes a threaded portion 38 for interconnection with arm 18, and a threaded portion 40 which interconnects with barrel 24. Carried within unit 22 is focusing lens 42. An inlet tube 44 is joined by interference fit with bore 46 and a cylindrical wall 48 of unit 22. At its free end 50, inlet 44 is connected to a hose 52 which is in turn connected to a purge gas source 54 which provides a gas such as $CO_2$ under gentle pressure to create a backflow from lens 42 forward into barrel 24. This keeps any debris from the vaporization from contacting and obscuring or damaging lens 42. Lens 42 is positioned directly in line with passage 56 provided in unit 22 for propagation of the laser beam. Threads 40 of lens unit 22 engage with threads 60 of barrel 24, FIG. 4, which also includes a passage 62 which communicates with laser aperture 26 to create a clear passage for the propagation of laser beam 20a to wall 66 of a beating heart. Lens 42 focuses the laser beam proximate aperture 26 and surface 32.

As can be seen clearly in FIG. 4, contact surface 32 is considerably broader than the cross-sectional area of barrel 24 alone and is formed in the shape of a flange with surface 32 being smooth and flat and all the edges rounded. This increases the area of contact with the heart, and therefore decreases the pressure or force per unit area on the heart. It also provides a more stable platform by which to maintain perpendicularity between the beam 28 and the heart wall 66. Thus this construction provides the necessary precision in locating the focus of the beam on the heart wall without interfering with the heart operation or its electrical activity. Barrel 24 includes vent holes 70, 72 for exhausting the purging gas and trapped debris away from the lens 42 and away from aperture 26.

Although barrel 24 has been shown as a straight member, this is not a necessary limitation of the invention. For example, barrel 24a, FIG. 5, may include a right angle configuration 80, so that surface 32a is facing at right angles to the path of the beam 28. A reflective surface 82 is provided to reflect the beam from an incoming path parallel to axis 84 to the outgoing path parallel to axis 86. One or more vent holes 88 are provided for exhausting the first gas.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A handpiece for use in a transmyocardial revascularization heart synchronized pulsed laser system comprising:
   a barrel having a passage for transmitting a laser beam; and
   a contacting wall at one end of said barrel including an aperture in communication with said passage and a face extending continuously radially outward from said aperture to the periphery of said contacting wall.

2. The handpiece of claim 1 further including means for focusing a laser beam transmitted through said passage to focus the laser beam proximate said aperture to vaporize the tissue of the heart wall and create a hole therein.

3. The handpiece of claim 2 in which said means for focusing focuses the laser beam beyond said contacting wall.

4. The handpiece of claim 2 in which said means focusing focuses the laser beam within said barrel.

5. The handpiece of claim 2 in which said means for focusing focuses the laser beam in said aperture.

6. The handpiece of claim 1 in which said contacting wall is broader in cross-sectional area than said barrel and said contacting wall is smooth and flat with all the edges rounded.

7. The handpiece of claim 1 further including means for introducing a gas to purge said passage of debris from the vaporized heart wall.

8. The handpiece of claim 7 further including exhaust means in communication with said passage for venting debris purged by the gas.

9. The handpiece of claim 8 in which said exhaust means is located proximate said aperture.

10. The handpiece of claim 1 in which said barrel is straight.

11. The handpiece of claim 1 in which said contacting wall is thermally insulating.

12. The handpiece of claim 1 in which said barrel is angled and includes deflecting means for directing a laser beam along the angled barrel.

13. The handpiece of claim 12, in which said deflecting means includes a mirror.

14. A handpiece for use in a transmyocardial revascularization heart synchronized pulsed laser system comprising:
   a barrel having a passage for transmitting a laser beam;

a contacting wall at one end of said barrel including an aperture in communication with said passage and a face extending continuously radially outward from said aperture to the periphery of said contacting wall; and means for focusing a laser beam transmitted through said passage to focus the laser beam proximate said aperture to vaporize the tissue of the heart wall and create a hole therein.

15. The handpiece of claim 14 in which said contacting wall includes a solid face.

16. The handpiece of claim 14 in which said contacting wall is and smooth and flat with all the edges rounded.

17. A handpiece for use in a transmyocardial revascularization heart synchronized pulsed laser system, the handpiece comprising:

a barrel having an internal passage for transmitting a laser beam; and a contacting wall extending transversely from one end of said barrel, said contacting wall having an aperture in communication with said passage of said barrel, said contacting wall having a face extending continuously radially outward from said aperture to the periphery of said contacting wall.

18. A handpiece for use in a transmyocardial revascularization heart synchronized pulsed laser system, the handpiece comprising:

a barrel having an internal passage for transmitting a laser beam; and a contacting wall at one end of said barrel including an aperture in communication with said passage and a face extending continuously radially outward from said aperture to the periphery of said contacting wall such that the combination of the barrel and the contacting wall acts as a handpiece for contacting a beating heart during use of a transmyocardial revascularization heart synchronized pulsed laser system.

\* \* \* \* \*